United States Patent
Luo et al.

(10) Patent No.: US 11,428,808 B2
(45) Date of Patent: Aug. 30, 2022

(54) ULTRASONIC DETECTION METHOD, ULTRASONIC DETECTION SYSTEM, AND RELATED APPARATUS

(71) Applicant: CLOUDMINDS (SHENZHEN) HOLDINGS CO., LTD., Guangdong (CN)

(72) Inventors: Lei Luo, Guangdong (CN); Qingwei Ji, Guangdong (CN)

(73) Assignee: CLOUDMINDS (SHENZHEN) HOLDINGS CO., LTD., Shenzhen (CN)

( * ) Notice: Subject to any disclaimer, the term of this patent is extended or adjusted under 35 U.S.C. 154(b) by 467 days.

(21) Appl. No.: 16/569,848

(22) Filed: Sep. 13, 2019

(65) Prior Publication Data

US 2020/0088872 A1    Mar. 19, 2020

(30) Foreign Application Priority Data

Sep. 13, 2018   (CN) .......................... 201811068585.5

(51) Int. Cl.
*G01H 9/00* (2006.01)
*G01N 29/24* (2006.01)
(Continued)

(52) U.S. Cl.
CPC ............. *G01S 15/42* (2013.01); *G01H 9/008* (2013.01); *G01N 29/24* (2013.01); *G01S 7/52053* (2013.01); *G01S 15/89* (2013.01)

(58) Field of Classification Search
CPC .... G01S 15/899; G01S 7/52053; G01S 15/42; G01S 15/89; G01S 15/8936;
(Continued)

(56) References Cited

U.S. PATENT DOCUMENTS 5,470,350 A * 11/1995 Buchholtz ............ A61B 8/0833
  601/3
6,248,074 B1 * 6/2001 Ohno ..................... A61B 8/463
  600/463
(Continued)

FOREIGN PATENT DOCUMENTS

CN   102824189 A   12/2012
CN   103961134 A    8/2014
(Continued)

OTHER PUBLICATIONS

Examination Report for Chinese Patent Application No. 201811068585.5 dated Dec. 28, 2020.
(Continued)

*Primary Examiner* — Jacques M Saint Surin
(74) *Attorney, Agent, or Firm* — Heslin Rothenberg Farley & Mesiti, PC

(57) ABSTRACT

Some embodiments of the present disclosure relate to the technical field of ultrasonic detection, and disclose an ultrasonic detection method, an ultrasonic detection system, and a related apparatus. The ultrasonic detection method includes: acquiring a reflected ultrasonic signal transmitted by an ultrasonic detector; generating an ultrasonic image according to the reflected ultrasonic signal, and displaying the ultrasonic image; acquiring information of a mark input by an operator based on the ultrasonic image; determining a marking position according to the information of the mark; transmitting the marking position to the ultrasonic detector, for the ultrasonic detector to indicate a corresponding position of the marking position on a surface of a detected object. The present disclosure resolves problems such as difficulty in operating on the surface of the detected object during ultrasonic detection and a low success rate of operation.

12 Claims, 7 Drawing Sheets

(51) Int. Cl.
*G01S 7/52* (2006.01)
*G01S 15/89* (2006.01)
*G01S 15/42* (2006.01)

(58) Field of Classification Search
CPC .. G01N 29/043; G01N 29/265; G01N 29/048; G01N 29/24; A61B 8/42; G01H 9/008
USPC .......................................................... 73/645
See application file for complete search history.

(56) References Cited

U.S. PATENT DOCUMENTS

| | | | |
|---|---|---|---|
| 9,046,413 B2 * | 6/2015 | Nielsen | G01J 3/463 |
| 9,884,150 B2 * | 2/2018 | Jho | A61B 5/064 |
| 2011/0299778 A1 | 12/2011 | Telkka | |

FOREIGN PATENT DOCUMENTS

| | | |
|---|---|---|
| CN | 104856763 A | 8/2015 |
| CN | 105873317 A | 8/2016 |
| CN | 106344153 A | 1/2017 |
| CN | 107260209 A | 10/2017 |
| CN | 207475940 U | 6/2018 |
| CN | 207545112 U | 6/2018 |
| JP | H03188837 A | 8/1991 |
| JP | H11299778 A | 11/1999 |
| JP | 2002336247 A | 11/2002 |
| JP | 2006238913 A | 9/2006 |
| JP | 2008284144 A | 11/2008 |
| JP | 2009077754 A | 4/2009 |
| JP | 2010229480 A | 10/2010 |
| JP | 2017060587 A | 3/2017 |

OTHER PUBLICATIONS

Examination Report for Japanese Patent Application No. 2019-116500 dated Aug. 24, 2020.
Office Action for Japanese Patent Application No. 201916650 dated Aug. 2, 2019.

* cited by examiner

ULTRASONIC DETECTION METHOD, ULTRASONIC DETECTION SYSTEM, AND RELATED APPARATUS

CROSS-REFERENCE TO RELATED DISCLOSURE

This application claims the priority benefit of Chinese Patent Application No. 201811068585.5 filed on Sep. 13, 2018 and entitled "ULTRASONIC DETECTION METHOD, ULTRASONIC DETECTION SYSTEM, AND RELATED APPARATUS", the disclosure of which is incorporated by reference herein in its entirety.

TECHNICAL FIELD

The present disclosure relates to the field of ultrasonic detection technologies, and in particular, to an ultrasonic detection method, an ultrasonic detection system, and a related apparatus.

BACKGROUND

Most of current ultrasonic detection devices are bulky professional equipment. There are a few ultrasonic detection devices whose sizes are relatively small and that may be held by hand to perform detection. However, an ultrasonic detection device as such has a structure in which a hand-held end is separated from a processing end, and a screen display is generally disposed at the processing end. In other words, when a hand-held ultrasonic detection device is being used to perform detection, one hand is required to hold the processing end with a screen, and the other hand is required to hold an ultrasonic hand-held end to perform detection.

In the process of studying the existing technology, inventors find that when using the hand-held ultrasonic detection device to perform detection, both hands are needed at the same time. For an ordinary ultrasonic detection, this method is feasible, but no free hand is available if an additional operation is required during the ultrasonic detection. For example, when an operation such as infusion needling or carotid puncture is required during the ultrasonic detection in accordance with an ultrasonic display, even if the processing end and the display end are put aside to release one hand, it is very difficult to carry out the operation because both a needling position and a current blood vessel's position on the screen need to be watched. A success rate is still relatively low, though higher than that in a case without ultrasonic assistance.

SUMMARY

A technical problem to be resolved in some embodiments of the present disclosure is to provide an ultrasonic detection method, an ultrasonic detection system, and a related apparatus, so as to resolve problems such as difficulty in operating on a surface of a detected object during ultrasonic detection and a low success rate of operation.

An embodiment of the present disclosure provides an ultrasonic detector, a marking light being disposed at an ultrasonic probe of the ultrasonic detector;

the marking light being configured to indicate a marking position on the surface of the object that is being detected and that contacts a detection surface of the ultrasonic probe.

An embodiment of the present disclosure further provides an ultrasonic detection method applied to an ultrasonic imager, the ultrasonic detection method including:

acquiring a reflected ultrasonic signal transmitted by an ultrasonic detector;

generating an ultrasonic image according to the reflected ultrasonic signal and displaying the ultrasonic image;

acquiring information of a mark input by an operator based on the ultrasonic image;

determining a marking position according to the information of the mark; and transmitting the marking position to the ultrasonic detector, for the ultrasonic detector to indicate a corresponding position of the marking position on a surface of a detected object.

An embodiment of the present disclosure provides an ultrasonic detection apparatus, including: a first acquiring module, a display module, a second acquiring module, a determining module, and a transmitting module;

the first acquiring module is configured to acquire a reflected ultrasonic signal transmitted by an ultrasonic detector;

the display module is configured to generate an ultrasonic image according to the reflected ultrasonic signal and display the ultrasonic image;

the second acquiring module is configured to acquire information of a mark input by an operator based on the ultrasonic image;

the determining module is configured to determine a marking position according to the information of the mark;

the transmitting module is configured to transmit the marking position to the ultrasonic detector, for the ultrasonic detector to indicate a corresponding position of the marking position on a surface of a detected object.

An embodiment of the present disclosure further provides an ultrasonic imager, including:

at least one processor; and a memory communicably connected with the at least one processor for storing instructions executable by the at least one processor, wherein execution of the instructions by the at least one processor causes the at least one processor to perform the foregoing ultrasonic detection method.

An embodiment of the present disclosure further provides a computer readable storage medium configured to store a computer program, the computer program, when being executed by the processor, implements the foregoing ultrasonic detection method.

An embodiment of the present disclosure further provides an ultrasonic detection system, including the foregoing ultrasonic detector and the ultrasonic imager.

Compared to the existing art, in embodiments of the present disclosure, the marking light is disposed at the ultrasonic probe of the ultrasonic detector to indicate the marking position on the surface of the object that is being detected and that contacts the detection surface of the ultrasonic probe. The marking position is determined after processing of the information of the mark that is input by the operator and that is acquired by the ultrasonic imager. The marking light indicates the marking position for the operator to determine an accurate marking position according to the indicated position, helping the operator perform other operations according to the marking position, and preventing an inability to determine an accurate operating position according to a displayed image as a result of viewing the ultrasonic display image during detection performed using the ultrasonic detection system, thereby reducing operation difficulty, increasing a success rate of operation for an operator, and improving user experience.

In addition, the ultrasonic detector further includes a pressure sensor and a processor. The pressure sensor is disposed at the detection surface. The pressure sensor is configured to: acquire a pressure value between the detection surface and the detected object and transmit the pressure value to the processor, and the processor is configured to determine, according to the acquired pressure value, whether a control signal is sent to the marking light. The control signal is used to control a turn-on state or a turn-off state of the marking light, the turn-on state or the turn-off state of the marking light being used to indicate the marking position.

The pressure value acquired by the pressure sensor is used to indicate whether the ultrasonic detector contacts the detected object, for the processor to send a control signal according to the pressure value to indicate the marking position through the marking light.

In addition, the ultrasonic sensor further includes a displacement sensor, the displacement sensor is disposed at the ultrasonic probe. The displacement sensor is configured to: acquire a relative displacement value generated when the ultrasonic probe translates along the surface of the detected object, and transmit the relative displacement value to the processor. The processor is further configured to update the control signal according to the acquired relative displacement value, and transmit the updated control signal to the marking light. The updated control signal is used to control the marking light to indicate the marking position that is updated according to the relative displacement value.

It is determined that the ultrasonic detector is displaced, and the updated marking position may be determined according to the displacement value, so that the indicated marking position always corresponds to an accurate marking position, further improving user experience.

Moreover, the marking light is disposed at an edge position of the detection surface, or the marking light is disposed at a position that is at a side of the ultrasonic probe and that is adjacent to the detection surface.

The marking light is disposed at a position at the side of the ultrasonic probe, so that the operator can obviously determine the indicating position, thereby improving user experience.

Besides, the marking light includes N indicator lights, N being a positive integer greater than 1.

Each inter-distance of the N indicator lights is equal.

A plurality of disposed indicator lights can improve position accuracy, so that the operator can determine an accurate indicating position according to the indicator lights, further improving user experience.

Furthermore, the information of the mark includes a marked pattern. The determining a marking position according to the information of the mark includes: determining a pixel position, in the ultrasonic image, of the marked pattern in the information of the mark; and determining a marking position of the pixel position on a detection surface according to a correspondence between the pixel position and the detection surface of the ultrasonic detector.

Furthermore, after determining the marking position of the pixel position on the detection surface, the ultrasonic detection method further includes: determining a coordinate position corresponding to the marking position on the detection surface; determining the marking light corresponding to the marking position according to a correspondence between the coordinate position on the detection surface and the marking light; determining a control signal according to the corresponding marking light; and transmitting the control signal to the ultrasonic detector.

BRIEF DESCRIPTION OF THE DRAWINGS

One or more embodiments are exemplarily described through figures in accompanying drawings corresponding to the one or more embodiments. These exemplary descriptions do not constitute any limitation on the embodiments. Elements having identical reference numerals in the accompanying drawings are represented as similar elements. Unless otherwise stated, the figures in the accompanying drawings do not constitute any proportional limitation.

DETAILED DESCRIPTION

To make the objectives, technical solutions, and advantages of this application more comprehensible, the following further describes some embodiments of this application in detail with reference to the accompanying drawings and embodiments. It should be understood that specific embodiments described herein are only used to explain this application and are not intended to limit this application. However, a person of ordinary skill in the art may understand that, in the embodiments of this application, to make readers better understand this application, many technical details are put forward. However, even if there are no these technical details and various changes and modifications based on the following embodiments, the technical solutions that this application claims to protect may be implemented.

Figure 1:
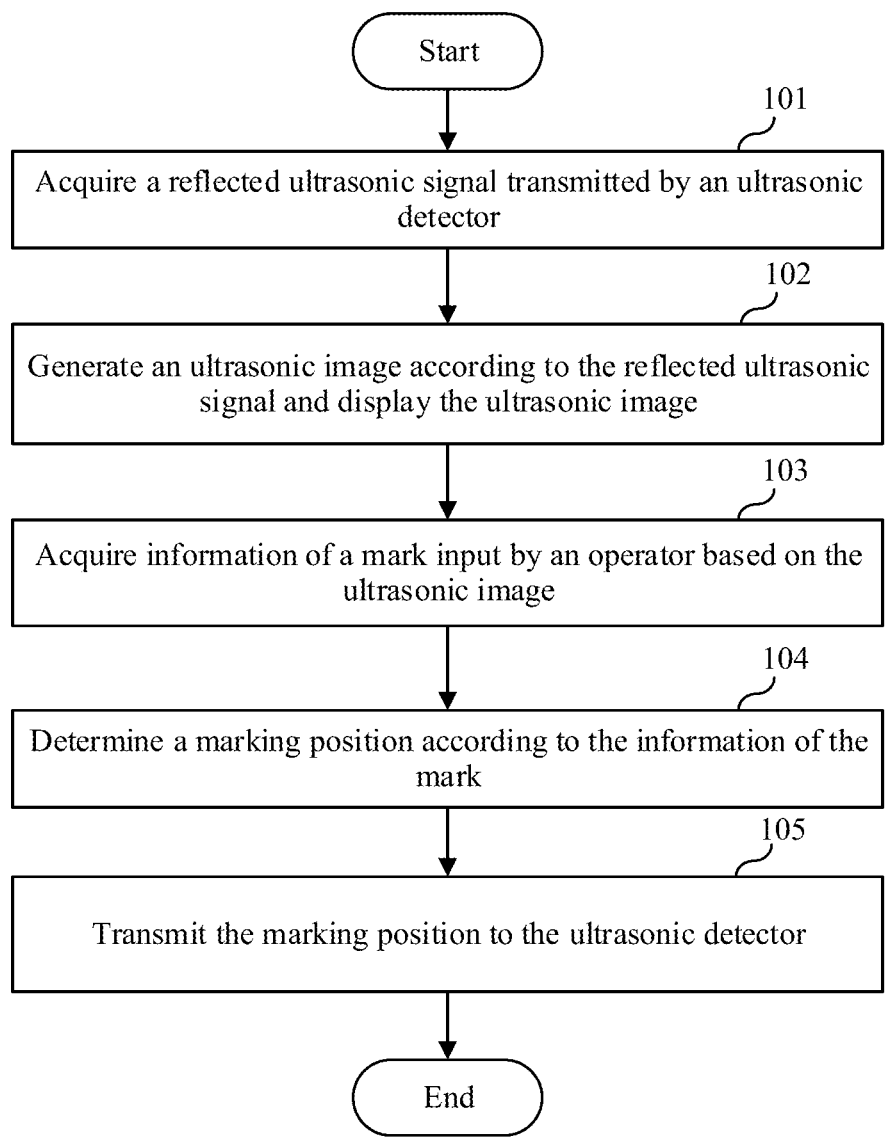
FIG. 1 is a flowchart of an ultrasonic detection method according to a first embodiment of the present disclosure.

A first embodiment of the present disclosure relates to an ultrasonic detection method applied to an ultrasonic imager, and an implementation process of the ultrasonic detection method is shown in FIG. 1. The implementation process includes the following steps.

Step 101: A reflected ultrasonic signal transmitted by an ultrasonic detector is acquired.

In particular, this embodiment is applied to the ultrasonic imager. The ultrasonic imager performs image processing according to the acquired reflected ultrasonic signal. The reflected ultrasonic signal may be acquired and transmitted to the ultrasonic imager by the ultrasonic detector, or may be acquired and transmitted to the ultrasonic imager by other devices. If the reflected ultrasonic signal is transmitted to the ultrasonic imager by the ultrasonic detector, the ultrasonic detector may directly transmit the acquired reflected ultrasonic signal to the ultrasonic imager, or may perform preprocessing on the acquired reflected ultrasonic signal and transmit the preprocessed reflected ultrasonic signal to the ultrasonic imager. Therefore, a type of the reflected ultrasonic signal acquired by the ultrasonic imager is not limited herein.

Step 102: An ultrasonic image is generated according to the reflected ultrasonic signal and is displayed.

In particular, a specific embodiment in which the ultrasonic imager generates an ultrasonic image after processing the reflected ultrasonic signal is similar to the known reflected ultrasonic signal imaging manner, and details are not described herein again.

If the ultrasonic imager acquires a reflected ultrasonic signal directly reflected to the ultrasonic detector, the ultrasonic imager performs image processing and displays an ultrasonic image after image processing. If the ultrasonic imager acquires a preprocessed reflected ultrasonic signal, the preprocessed reflected ultrasonic signal is processed correspondingly to generate an ultrasonic image, and the ultrasonic image is displayed.

Step 103: Information of a mark input by an operator based on the ultrasonic image is acquired.

In particular, the operator inputs the information of the mark to the ultrasonic imager based on an input device of the ultrasonic imager. The operator may view the ultrasonic image on a display, and mark the ultrasonic image. If a display screen of the ultrasonic imager can acquire the information of the mark input by the operator, for example, the display screen is a touch screen, the operator may directly input the information of the mark on the display screen. For example, the operator may input the information of the mark on the touch screen with a finger or a touch pen. If other input devices, such as a mouse or a keyboard, etc., are disposed for the ultrasonic imager, the operator may input, by dragging the mouse or using the keyboard, a control command to input the information of the mark in the ultrasonic imager. Therefore, a manner in which the operator inputs the information of the mark is not specifically limited in this embodiment.

In addition, the information of the mark input by the operator is also not specifically limited herein. For example, if the operator is a medical staff, and the operator performs an operation such as puncturing or needling, etc. according to a mark in the displayed image, the information of the mark may be a straight line for marking a blood vessel position or other symbols for marking an operating position. In particular, actual information of a mark shall prevail, and the information of the mark herein is merely an example for description.

In particular, the ultrasonic imager may process the acquired information of a mark in real time. For example, the acquired information of a mark is processed in real time and transmitted to a corresponding ultrasonic detector, and the ultrasonic detector performs marking according to a real-time control command. Alternatively, the ultrasonic imager processes and outputs the information of the mark after determining the information of the mark input by the operator. For example, a user inputs the information of the mark on a screen and inputs the information of the mark to the ultrasonic imager with a hand or a touch pen. While the operator inputs the information of the mark on the touch screen, the ultrasonic imager is processing the information of the mark. Alternatively, after the user determines the input information of the mark, the user may determine that, using a determining command input by the operator, information of the mark is completed by the operator, and then the information of the mark is processed and output. A specific manner of processing the ultrasonic imager is not limited herein.

Step 104: A marking position is determined according to the information of the mark.

In particular, the information of the mark includes a marked pattern. Specific implementation of determining a corresponding marking position on the ultrasonic probe according to the marking pattern is as follows: a pixel position, in the ultrasonic image, of the marking pattern in the information of the mark is determined; and a marking position of the pixel position in a detection surface is determined according to a correspondence between the pixel position and the detection surface of the ultrasonic detector.

It should be noted that the marking position determined according to the information of the mark may be a marking position on the displayed image, or may be a marking position on the ultrasonic probe, which is not specifically limited herein.

If the marking position on the displayed image is determined according to the information of the mark, the ultrasonic probe determines, according to a position correspondence between the displayed image and the detection surface of the ultrasonic probe, a position marked on the ultrasonic detection surface.

Figure 2:
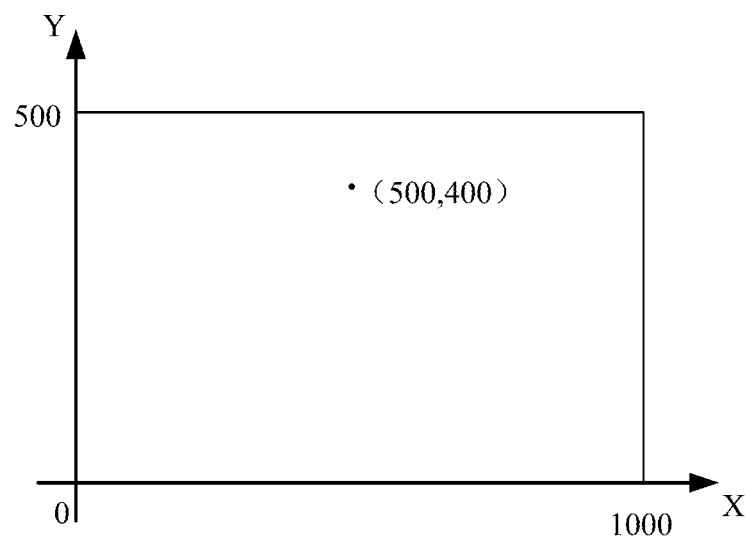
FIG. 2 is a schematic diagram of information of a mark according to a first embodiment of the present disclosure.
Figure 3:
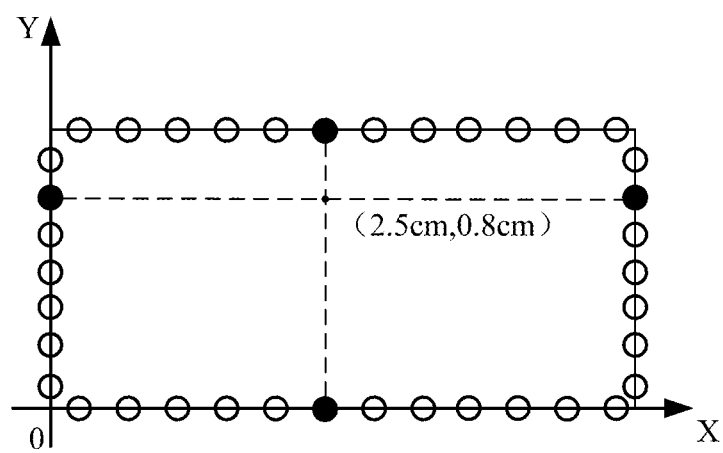
FIG. 3 is a schematic diagram of a marking position indicated by a detection probe according to a first embodiment of the present disclosure.

It is determined that the pixel position of the marked pattern in the information of the mark is an absolute position of the marked pattern. A corresponding absolute position on the ultrasonic probe may be determined according to the absolute position of the marked pattern. For example, a real pixel of an image is 1000×500, and a size of an actual imaging element of the probe is 5×1 (centimeter). If the marked pattern is a point, and a pixel position of the point on the image is (500, 400), which is shown in FIG. 2, a corresponding position on the ultrasonic probe is (2.5 cm, 0.8 cm), which is shown in FIG. 3. It should be noted that, in FIG. 3, an example in which marking lights are disposed at an edge position of the detection probe is used for description, and a filled marking light is used to indicate a marking light in a turn-on state. In FIG. 3, turned-on marking lights are used to indicate a marking position. A specific process of determining a corresponding actual marking position on the ultrasonic probe using the pixel position of the marked pattern in the information of the mark is not limited herein. When a specific position is being determined using an image pixel, because the number of indicator lights on the ultrasonic probe is limited, specific pixel positions cannot completely correspond to coordinates of the indicator lights. Therefore, it is determined that a marking light corresponding to a closest coordinate position indicates the coordinate position. In addition, the determining of an image pixel position may be performed in other manners, which is not limited herein.

Step 105: The marking position is transmitted to the ultrasonic detector.

After the ultrasonic detector acquires the marking position, the ultrasonic detector indicates a corresponding position of the marking position on the surface of the detected object.

In particular, data transmission between the ultrasonic detector and the ultrasonic imager may be wired data transmission or wireless data transmission. A specific connection between the ultrasonic detector and the ultrasonic imager is not limited herein.

It is worth mentioning that the foregoing ultrasonic detection method applied to the ultrasonic imager may be applied to an ultrasonic detection device for human detection, or may be applied to an ultrasonic detection device for ultrasonic flaw detection in device detection, which is not specifically limited herein.

Compared to the existing art, the marking light is disposed at the ultrasonic probe of the ultrasonic detector to indicate the marking position on the surface of the object that is being detected and that contacts the detection surface of the ultrasonic probe. The marking position is determined after processing of the information of the mark that is input by the operator and that is acquired by the ultrasonic imager. The marking light indicates the marking position for the operator to determine the accurate marking position according to an indicated position, helping the operator perform other operations according to the marking position, and preventing an inability to determine an accurate operating position according to a displayed image as a result of viewing the ultrasonic display image during detection performed using the ultrasonic detection system, thereby reducing operation difficulty, increasing a success rate of operation for an operator, and improving user experience.

Figure 4:
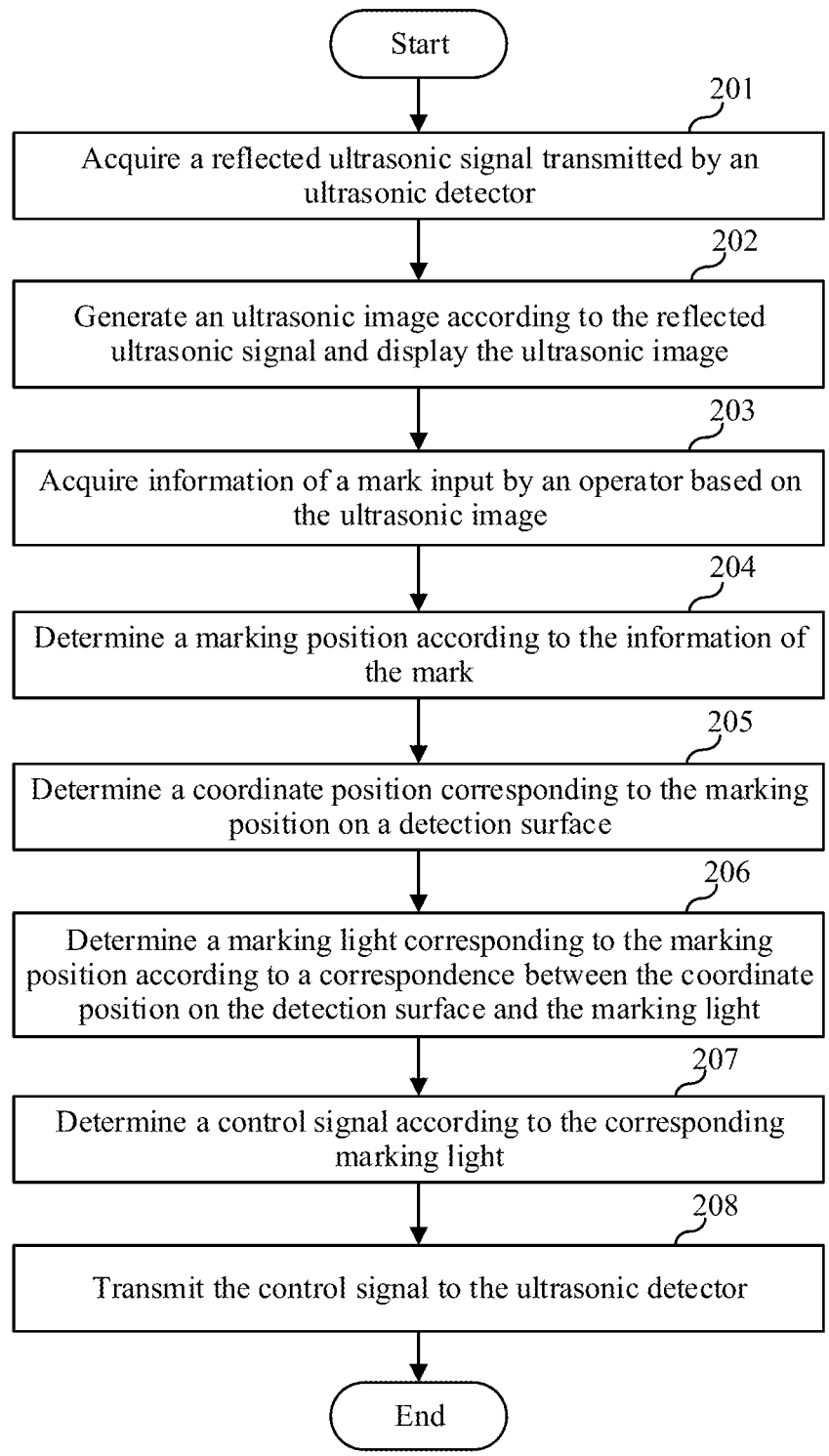
FIG. 4 is a flowchart of an ultrasonic detection method according to a second embodiment of the present disclosure.

A second embodiment of the present disclosure relates to an ultrasonic detection method. The second embodiment is roughly the same as the first embodiment, and a main difference lies in that an implementation of determining a state of the marking light according to the marking position is described in detail in the second embodiment of the present disclosure. A process of the method of the second embodiment is shown in FIG. 4, including step 201 to step 208. Step 201 to step 204 are the same as step 101 to step 104 in the first embodiment, and are not described herein again. Only the difference is described herein.

It should be noted that a state of the marking light corresponding to the marking position may be determined by the processor disposed in the ultrasonic imager, or may be determined by the ultrasonic detector. An example in which determining is performed by the ultrasonic imager is used herein, but it is not limited that determining must be performed by the ultrasonic imager in step 205 to step 208.

Step 205: A coordinate position corresponding to the marking position on the detection surface is determined.

Step 206: A marking light corresponding to the marking position is determined according to a correspondence between the coordinate position on the detection surface and the marking light.

Step 207: A control signal is determined according to the corresponding marking light.

Step 208: The control signal is transmitted to the ultrasonic detector.

In particular, the marking light at the ultrasonic detector is configured to indicate the marking position. Therefore, a coordinate position corresponding to the marking position on the detection surface is required to be determined, to help the marking light indicate the coordinate position.

The correspondence between the marking light and the coordinate position on the detection surface is related to the number and a position of the marking light. However, once the marking light is fixedly disposed, the coordinate position on the detection surface may be also determined. The correspondence between the coordinate position on the detection surface and the marking light is pre-stored in a memory of the ultrasonic imager, so that the processor acquires the correspondence between the coordinate position on the detection surface and the marking light, and then determines the marking light corresponding to the marking position, to determine positions of marking lights to be turned on and turned off.

In particular, after determining the marking lights to be turned on and turned off, the processor sends a control signal according to the marking position. The control signal may be respectively transmitted to each marking light, or a serial interface of a same communication terminal that a plurality of marking lights are jointly connected to, and each marking light acquires the control signal through the serial interface.

Division of the steps of the foregoing various methods are merely for clear description. During implementation, the steps may be combined into one step, or some steps may be divided into a plurality steps, and the steps including a same logic relationship shall fall within the protection scope of the present disclosure. Insignificant modification added or an insignificant design introduced to an algorithm or a process without changing a core design of the algorithm and process shall fall within the protection scope of the present disclosure.

Figure 5:
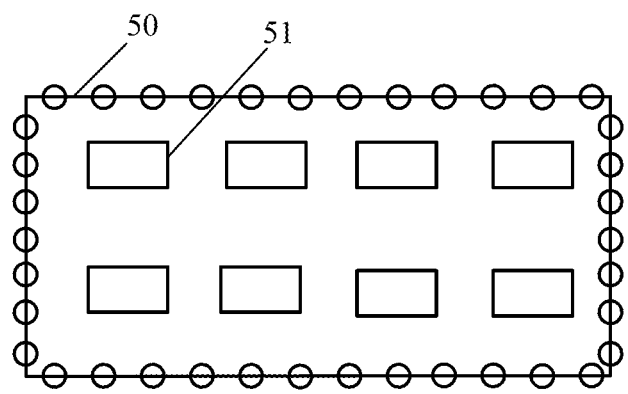
FIG. 5 is a schematic structural diagram of an ultrasonic detector according to a third embodiment of the present disclosure.

A third embodiment of the present disclosure relates to an ultrasonic detector, and a structure thereof is shown in FIG. 5. A marking light 50 is disposed at an ultrasonic probe of the ultrasonic detector, the marking light 50 being configured to indicate a marking position on a surface of an object that is being detected and that contacts a detection surface of the ultrasonic probe.

In particular, the marking light 50 is configured to indicate the marking position. The marking light 50 includes N indicator lights in a turn-on state or a turn-off state, and position information is indicated according to a current state of the indicator lights. N is a positive integer greater than 1, and inter-distances among the N indicator lights are equal.

In particular, a specific manner of arranging the marking light 50 is shown in FIG. 5. The marking light 50 is disposed at an edge position of the detection surface. An ultrasonic detection probe 51 is further disposed on the ultrasonic probe, the ultrasonic detection probe 51 being configured to transmit an ultrasonic signal or receive a reflected ultrasonic signal. It should be noted that more indicator lights disposed at the edge of the ultrasonic detection surface bring a more accurate marking position indicated by the indicator lights. The indicator lights are evenly distributed at the edge position of the detection surface. In addition, the indicator lights may be unevenly distributed. For example, there are more indicator lights at some positions and less indicator lights at other positions. When there are sufficient light sources and a density is large enough, the marking light 50 may be equivalent to a circular organic light-emitting diode (OLED) display screen.

The marking light 50 may be further disposed at a position that is at a side of the ultrasonic probe and that is adjacent to the detection surface, so that an operator determines, according to a turn-on state or a turn-off state of the marking light 50, a marking position indicated by the marking light 50. It should be noted that a specific position of the marking light 50 is not limited herein, and the above is merely an example for description but not used to limit the position of the marking light 50.

In particular, when indicating the marking position, the ultrasonic detector acquires the marking position from an ultrasonic imager. If the marking position includes states of various marking lights 50 at the ultrasonic probe, the marking position is transmitted to the marking light 50, to control the marking light 50 to be in a turn-on state or a turn-off state. If the marking position includes a coordinate position on the ultrasonic probe, a processor in the ultrasonic detector generates control information according to the coordinate position. The control information is used to determine states of various marking lights 50, and the control information is transmitted to a corresponding marking light 50 to indicate the marking position.

It should be noted that a pressure sensor and a processor are disposed for the ultrasonic detector to facilitate control of a time at which the marking light is turned on or turned off. When the marking light 50 at the ultrasonic detector indicates the marking position, it needs to be determined that the ultrasonic probe is attached to a surface of a detected object. In particular, the pressure sensor is disposed at a detection surface. The pressure sensor acquires a value of a pressure between the detection surface and the detected object, and transmits the pressure value to the processor. The processor determines whether a control signal is sent to the marking light 50 according to the acquired pressure value. The control signal is used to control the marking light 50 to be in a turn-on state or a turn-off state, the turn-on state or the turn-off state of the marking light 50 being used to indicate the marking position.

A preset pressure value may be set to determine whether the ultrasonic probe contacts the detected object, and the marking light 50 is triggered using the preset pressure value. For example, the preset value may be 0. If the pressure value acquired by the pressure sensor is 0, it indicates that the ultrasonic probe does not contact the detected object, and the marking light 50 cannot indicate the marking position on the surface of the detected object. Therefore, the marking light 50 is prevented from being turned on. If the pressure value acquired by the pressure sensor is not 0, it indicates that the ultrasonic probe closely contacts the detected object, and the marking light 50 can indicate the marking position on the surface of the detected object. Therefore, triggering turn-on of the marking light 50 when it is determined that the ultrasonic detector closely contacts the detected object can accurately indicate the marking position.

Compared to the existing art, the marking light in the ultrasonic detector in this embodiment can indicate the marking position, preventing an inability to determine an accurate operating position according to a displayed image as a result of viewing the ultrasonic display image during detection performed using the ultrasonic detection system, thereby increasing a success rate of operation for an operator and improving user experience.

Figure 6:
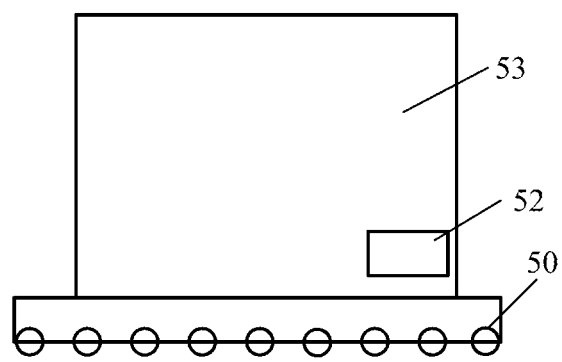
FIG. 6 is a schematic structural diagram of an ultrasonic detector according to a fourth embodiment of the present disclosure.

A fourth embodiment of the present disclosure relates to an ultrasonic detector. The fourth embodiment is roughly the same as the third embodiment, and a main difference lies in that a displacement sensor in the ultrasonic detector is described in detail in the fourth embodiment of the present disclosure. As shown in FIG. 6, the ultrasonic detector further includes a displacement sensor 52.

In particular, the displacement sensor 52 is disposed at an ultrasonic probe 53. The displacement sensor 52 is configured to: acquire a relative displacement value generated when the ultrasonic probe translates along a surface of a detected object, and transmit the relative displacement value to a processor. The processor updates a control signal according to the acquired relative displacement value, and transmits the updated control signal to a marking light 50. The updated control signal is used to control the marking light 50 to indicate the marking position that is updated according to the relative displacement value.

If displacement occurs when the ultrasonic detector indicates the marking position, the marking position may be inaccurately indicated. In order to prevent repeated determining of the marking position, the updated marking position is determined according to displacement amount of the displacement sensor, so that a time for determining the updated marking position can be reduced and working efficiency of the ultrasonic detector can be improved. In particular, the processor acquires a displacement amount of the displacement sensor along a direction, and correspondingly changes a state of an indicator light. For example, a coordinate corresponding to an original marking position in FIG. 3 is (2.5 cm, 0.8 cm). The displacement sensor detects that the ultrasonic probe moves leftward for 1 cm, and moves upward for 0.3 cm, and determines that an updated coordinate of the original coordinate is (3.5 cm, 0.5 cm). The processor adjusts a state of the indicator light according to the updated coordinate, to ensure information of the mark on a displayed image keeps unchanged. If the marking position is not within a range covered by the detection surface after movement of the displacement sensor of the detection probe, the indicator lights are all turned off.

It should be noted that the foregoing embodiment in which the updated coordinate position is determined according to the displacement sensor is merely an example for description, and is not specifically limited.

Figure 7:
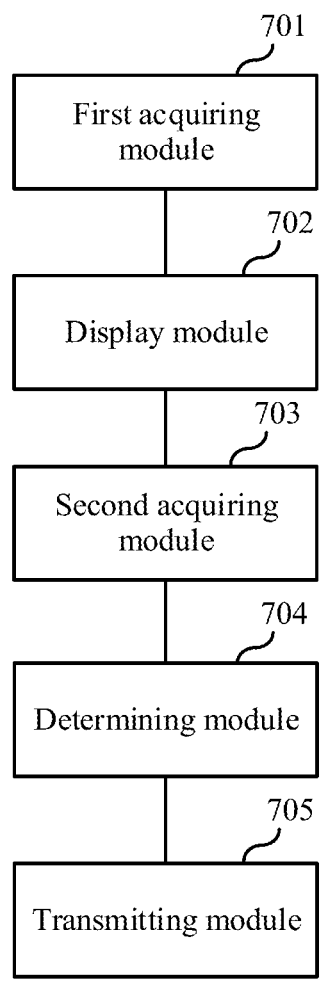
FIG. 7 is a schematic structural diagram of an ultrasonic detection apparatus according to a fifth embodiment of the present disclosure.

A fifth embodiment of the present disclosure relates to an ultrasonic detection apparatus. As shown in FIG. 7, the ultrasonic detection apparatus includes: a first acquiring module 701, a display module 702, a second acquiring module 703, a determining module 704, and a transmitting module 705.

The first acquiring module 701 is configured to acquire a reflected ultrasonic signal transmitted by an ultrasonic detector.

The display module 702 is configured to generate an ultrasonic image according to the reflected ultrasonic signal and display the ultrasonic image.

The second acquiring module 703 is configured to acquire information of a mark input by an operator based on the ultrasonic image.

The determining module 704 is configured to determine a marking position according to the information of the mark.

The transmitting module 705 is configured to transmit the marking position to the ultrasonic detector, for the ultrasonic detector to indicate a corresponding position of the marking position on a surface of a detected object.

It is not difficult to find that this embodiment is a system embodiment corresponding to the first embodiment, and this embodiment may be combined with the first embodiment for implementation. Related technical details mentioned in the first embodiment are still valid in this embodiment and are not described herein again to reduce repetition. Correspondingly, related technical details mentioned in this embodiment may also be applied to the first embodiment.

It is worth mentioning that related various modules in this embodiment are all logic modules. In actual application, a logical unit may be a physical unit, or may be a part of the physical unit, or may be implemented using a combination of a plurality of physical units. In addition, in order to highlight an innovative part of the present disclosure, a unit not closely related to resolving of the technical problems mentioned in the present disclosure is not introduced in this embodiment. However, it does not mean that there are no other units in this embodiment.

Figure 8:
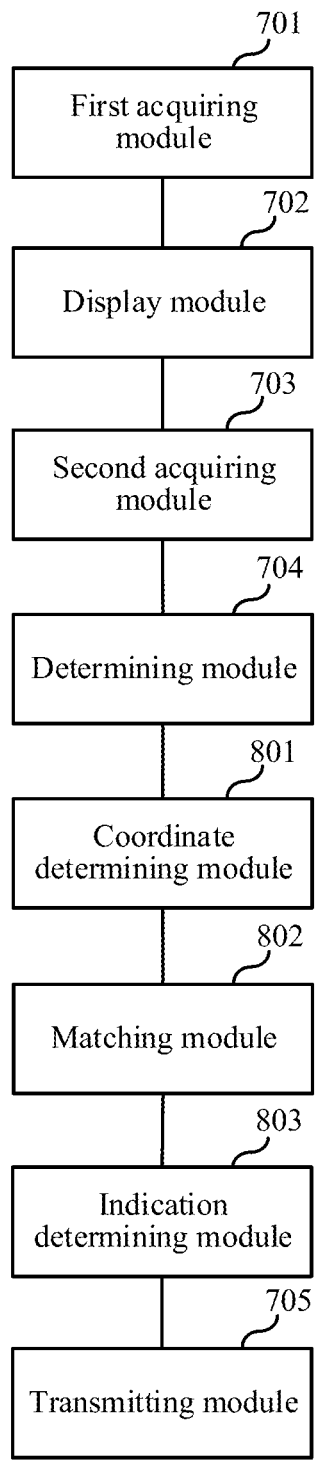
FIG. 8 is a schematic structural diagram of an ultrasonic detection apparatus according to a sixth embodiment of the present disclosure.

A sixth embodiment of the present disclosure relates to an ultrasonic detection apparatus. The sixth embodiment is roughly the same as the third embodiment, and a main difference lies in that: in the sixth embodiment of the present disclosure, that the ultrasonic detection apparatus further includes a coordinate determining module 801, a matching module 802, and an indication determining module 803 is further specifically described, which is shown in FIG. 8.

The coordinate determining module 801 is configured to determine a coordinate position corresponding to a marking position on a detection surface.

The matching module 802 is configured to determine, according to a correspondence between the coordinate position on the detection surface and a marking light, a marking light corresponding to the marking position.

The indication determining module 803 is configured to determine a control signal according to the corresponding marking light.

The transmitting module 705 is further configured to determine the control signal according to the corresponding marking light.

Since the second embodiment corresponds to this embodiment, this embodiment may be combined with the second embodiment for implementation. Related technical details mentioned in the second embodiment are still valid in this embodiment, and a technical effect achieved in the second embodiment may be also achieved in this embodiment, which are not described herein again to reduce repetition. Correspondingly, related technical details mentioned in this embodiment may be also applied to the second embodiment.

Figure 9:
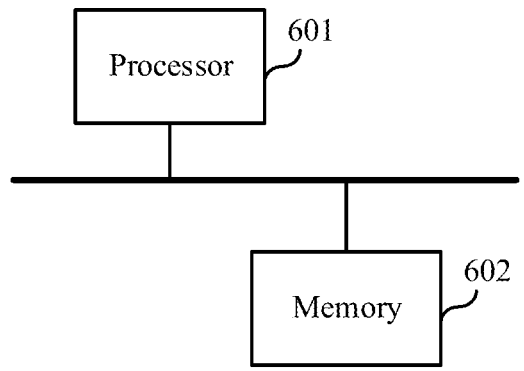
FIG. 9 is a schematic structural diagram of an ultrasonic imager according to a seventh embodiment of the present disclosure.

A seventh embodiment of the present disclosure relates to an ultrasonic imager. As shown in FIG. 9, the ultrasonic imager includes at least one processor 601 and a memory 602 communicatively connected to the at least one processor 601. The memory 602 stores instructions executable by the at least one processor 601, and the instructions are executed by the at least one processor 601 to cause the at least one processor 601 to perform an ultrasonic detection method.

In this embodiment, that the processor 601 is a central processing unit (CPU) is used as an example, and that the memory 602 is a random access memory (RAM) is used as an example. The processor 601 and the memory 602 may be connected through a bus or in other manners. In FIG. 9, that the processor 601 and the memory 602 are connected through a bus is used as an example. The memory 602, as a non-volatile computer readable storage medium, may be configured to store a non-volatile software program and non-volatile computer-executable program and module. For example, a program that implements the ultrasonic detection method in the embodiments of the present disclosure is stored in the memory 602. The processor 601 runs the non-volatile software program, instruction, and module stored in the memory 602, to perform various functional application programs of a device and data processing, that is, implements the foregoing ultrasonic detection method.

The memory 602 may include a program storage area and a data storage area. The program storage area may store an operating system and an application program required for at least one function, and the data storage area may store an option list and the like. In addition, the memory may include a high speed random access memory, and may further include a non-volatile memory, such as at least one magnetic disk memory device, a flash memory device, or other non-volatile solid state memory devices. In some embodiments, the memory 602 may optionally include remotely disposed memories relative to the processor 601, and these remote memories may be connected to an external device via a network. Examples of the foregoing network includes, but is not limited to, an Internet, an intranet, a local area network, a mobile communication network, and a combination thereof.

One or more program modules are stored in the memory 602. When the one or more program modules are executed by one or more processors 601, the ultrasonic detection method in the foregoing first method embodiment or second method embodiment is performed.

The foregoing products can perform the ultrasonic detection method provided in the embodiments of the present disclosure, and have corresponding functional modules for performing the method and beneficial effects. For technical details not described in detail in this embodiment, refer to the ultrasonic detection method provided in the embodiments of the present disclosure.

An eighth embodiment of the present disclosure relates to a computer readable storage medium. The readable storage medium is a computer readable storage medium, and computer instructions are stored in the computer readable storage medium. The computer instructions cause a computer to perform the ultrasonic detection method in the first method embodiment or the second method embodiment of the present disclosure.

Figure 10:
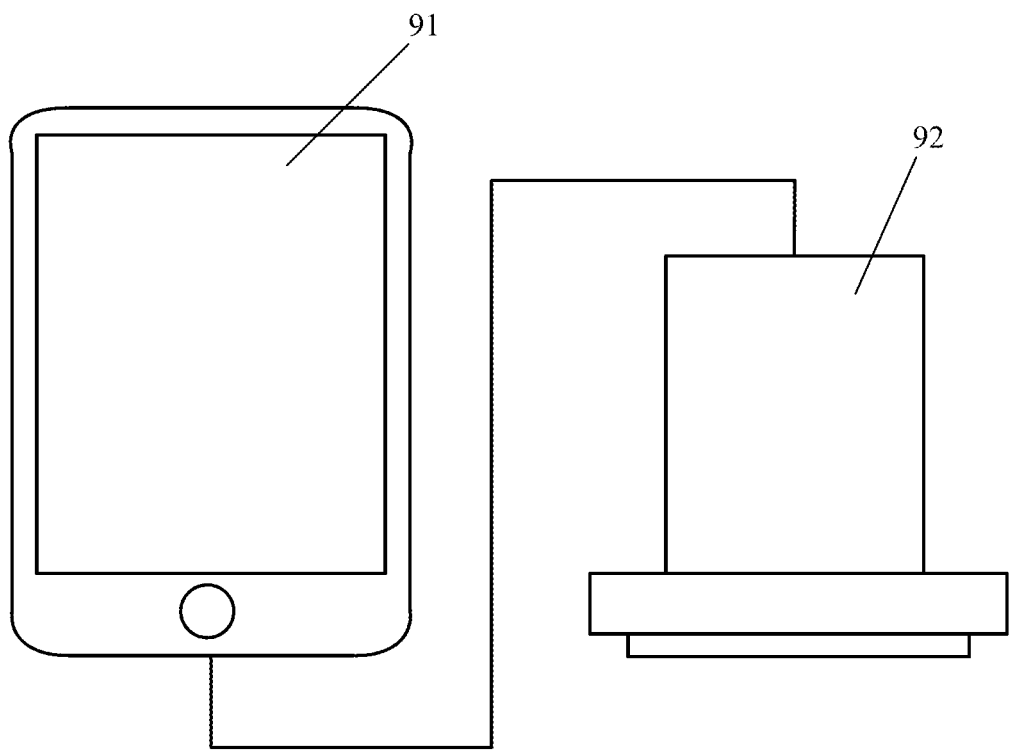
FIG. 10 is a schematic structural diagram of an ultrasonic imaging system according to a ninth embodiment of the present disclosure.

A ninth embodiment of the present disclosure relates to an ultrasonic detection system. As shown in FIG. 10, the ultrasonic detection system includes the ultrasonic detector 91 in the foregoing third embodiment or fourth embodiment and the ultrasonic imager 92 in the seventh embodiment.

In particular, the ultrasonic detection system may be an ultrasonic apparatus applied to human body examination, or may be an ultrasonic apparatus applied to ultrasonic flaw detection of an element. Specific application is not limited herein.

Persons skilled in the art can understand that, all or some of the steps of the method according to the foregoing embodiments may be implemented by a program instructing relevant hardware. The program is stored in a storage medium, and contains several instructions used to instruct a device (which may be a single-chip microcomputer, a chip, or the like) to perform all or some steps of the methods in the embodiments of this application. The foregoing storage medium includes: any medium that can store program code, such as a USB flash drive, a removable hard disk, a read-only memory (ROM, Read-Only Memory), a random access memory (RAM, Random Access Memory), a magnetic disk, or an optical disc.

A person of ordinary skill in the art may understand that, the foregoing embodiments are specific embodiments for implementing the present invention. However, during actual application, various changes may be made to the embodiments in form and detail without departing from the spirit and scope of the present invention.

What is claimed is:

1. An ultrasonic detector, wherein a marking light is disposed at an ultrasonic probe of the ultrasonic detector;
    the marking light is configured to indicate a marking position on a surface of a detected object that contacts a detection surface of the ultrasonic probe;
    wherein the ultrasonic detector further comprises a pressure sensor and a processor, the pressure sensor is disposed at the detection surface; the pressure sensor is configured to acquire a pressure value between the detection surface and the detected object and transmit the pressure value to the processor; the processor is configured to determine, according to the acquired pressure value, whether a control signal is transmitted to the marking light; wherein, the control signal is used to control the marking light to be in a turn-on state or a turn-off state, the turn-on state or the turn-off state of the marking light being used to indicate the marking position.

2. The ultrasonic detector according to claim 1, wherein the ultrasonic detector further comprises a displacement sensor, the displacement sensor is disposed at the ultrasonic probe;

the displacement sensor is configured to acquire a relative displacement value generated when the ultrasonic probe translates along the surface of the detected object, and transmit the relative displacement value to the processor;

the processor is further configured to update the control signal according to the acquired relative displacement value, and transmit the updated control signal to the marking light; wherein the updated control signal is used to control the marking light to indicate the marking position that is updated according to the relative displacement value.

3. The ultrasonic detector according to claim 2, wherein the marking light is disposed at an edge position of the detection surface, or the marking light is disposed at a position that is at a side of the ultrasonic probe and that is adjacent to the detection surface.

4. The ultrasonic detector according to claim 2, wherein the marking light comprises N indicator lights, N being a positive integer greater than 1.

5. The ultrasonic detector according to claim 4, wherein distances between adjacent indicator lights of the N indicator lights are equal.

6. The ultrasonic detector according to claim 1, wherein the marking light is disposed at an edge position of the detection surface, or the marking light is disposed at a position that is at a side of the ultrasonic probe and that is adjacent to the detection surface.

7. The ultrasonic detector according to claim 1, wherein the marking light comprises N indicator lights, N being a positive integer greater than 1.

8. The ultrasonic detector according to claim 7, wherein distances between adjacent indicator lights of the N indicator lights are equal.

9. An ultrasonic detection method applied to an ultrasonic imager, wherein the ultrasonic detection method comprises:

acquiring a reflected ultrasonic signal transmitted by an ultrasonic detector;

generating an ultrasonic image according to the reflected ultrasonic signal and displaying the ultrasonic image;

acquiring information of a mark input by an operator based on the ultrasonic image;

determining a marking position according to the information of the mark; and transmitting the marking position to the ultrasonic detector, for the ultrasonic detector to indicate a corresponding position of the marking position on a surface of a detected object, wherein the information of the mark comprises a marked pattern; and the determining the marking position according to the information of the mark comprises determining a pixel position, in the ultrasound image, of the marked pattern in the information of the mark, and determining a marking position of the pixel position on a detection surface according to a correspondence between the pixel position and the detection surface of the ultrasonic detector.

10. The ultrasonic detection method according to claim 9, wherein after the determining the marking position of the pixel position on the detection surface, the ultrasonic detection method further comprises:

determining a coordinate position corresponding to the marking position on the detection surface;

determining the marking light corresponding to the marking position according to a correspondence between the coordinate position on the detection surface and the marking light;

determining a control signal according to the corresponding marking light; and transmitting the control signal to the ultrasonic detector.

11. An ultrasonic imager, comprising:

at least one processor; and a memory communicably connected with the at least one processor;

wherein the memory stores an instruction executable by the at least one processor, when the instruction is executed by the at least one processor, causing the at least one processor to perform an ultrasonic detection method comprising:

acquiring a reflected ultrasonic signal transmitted by an ultrasonic detector;

generating an ultrasonic image according to the reflected ultrasonic signal and displaying the ultrasonic image;

acquiring information of a mark input by an operator based on the ultrasonic image;

determining a marking position according to the information of the mark; and transmitting the marking position to the ultrasonic detector, for the ultrasonic detector to indicate a corresponding position of the marking position on a surface of a detected object;

wherein the information of the mark comprises a marked pattern; and the determining the marking position according to the information of the mark comprises determining a pixel position, in the ultrasound image, of the marked pattern in the information of the mark, and determining a marking position of the pixel position on a detection surface according to a correspondence between the pixel position and the detection surface of the ultrasonic detector.

12. The ultrasonic imager according to claim 11, wherein after the determining the marking position of the pixel position on the detection surface, the ultrasonic detection method further comprises:

determining a coordinate position corresponding to the marking position on the detection surface;

determining the marking light corresponding to the marking position according to a correspondence between the coordinate position on the detection surface and the marking light;

determining a control signal according to the corresponding marking light; and transmitting the control signal to the ultrasonic detector.

* * * * *